(12) United States Patent  
Pompilio, III et al.

(10) Patent No.: US 8,814,359 B1  
(45) Date of Patent: Aug. 26, 2014

(54) MEMORY RECOLLECTION TRAINING SYSTEM AND METHOD OF USE THEREOF

(75) Inventors: Daniel V. Pompilio, III, Smyrna, GA (US); Jason Zamer, Atlanta, GA (US); Chantal Kerssens, Atlanta, GA (US); Tim Sebel, Atlanta, GA (US)

(73) Assignee: SimpleC, LLC, Atlanta, GA (US)

( * ) Notice: Subject to any disclaimer, the term of this patent is extended or adjusted under 35 U.S.C. 154(b) by 235 days.

(21) Appl. No.: 13/447,877

(22) Filed: Apr. 16, 2012

Related U.S. Application Data

(63) Continuation-in-part of application No. 13/330,779, filed on Dec. 20, 2011, which is a continuation of application No. 12/243,404, filed on Oct. 1, 2008, now Pat. No. 8,096,657.

(60) Provisional application No. 61/475,285, filed on Apr. 14, 2011, provisional application No. 60/997,168, filed on Oct. 1, 2007.

(51) Int. Cl.  
*A61B 3/02* (2006.01)  
*A61B 3/032* (2006.01)  
*A61B 3/18* (2006.01)  
*A61H 5/00* (2006.01)

(52) U.S. Cl.  
CPC . *A61B 3/02* (2013.01); *A61B 3/032* (2013.01); *A61B 3/18* (2013.01); *A61H 5/00* (2013.01)  
USPC ............................. 351/223; 351/203; 351/238

(58) Field of Classification Search  
CPC .... A61B 3/0016; A61B 3/0041; A61B 3/005; A61B 3/02; A61B 3/032; A61B 3/18; A61H 5/00  
USPC ......... 351/200, 205, 222, 223, 237, 238, 246, 351/203, 23  
See application file for complete search history.

(56) References Cited

U.S. PATENT DOCUMENTS

| 5,657,256 A | 8/1997 | Swanson et al. |
| 2012/0214143 A1* | 8/2012 | Severson et al. ............... 434/236 |

* cited by examiner

*Primary Examiner* — Huy K Mai  
(74) *Attorney, Agent, or Firm* — Nilay J. Choksi; Smith & Hopen, P.A.

(57) ABSTRACT

Graphical first individual interfaces, systems and methods of implementing an adaptable, interactive educational tool that provides cognitive and social benefits. An embodiment can be configured to provide a graphical first individual interface for presenting text and related content associated with a predetermined general subject matter. The specific text and related content presented to the first individual may be determined after baseline tests and related use are recorded to calculate the first individual's cognitive wellness. The present invention also provides social benefit by integrating a first individual's social network for uses in communication with the first individual's social network and in recalling the first individual's social network. The present invention further includes a unique algorithm for personalizing information and methodologies of implementing and displaying the educational tool to a first individual thereof.

17 Claims, 8 Drawing Sheets

MEMORY RECOLLECTION TRAINING SYSTEM AND METHOD OF USE THEREOF

CROSS-REFERENCE TO RELATED APPLICATIONS

This application claims priority to U.S. Provisional Application No. 61/475,285, entitled "Memory Recollection Training System", filed on Apr. 14, 2011, the contents of which are incorporated herein by reference in its entirety. This application also is a continuation-in-part of currently pending U.S. patent application Ser. No. 13/330,779, filed on Dec. 20, 2011, entitled "Systems and Methods for Aiding Computing Users Having Sub-Optimal Ability", which is a continuation of U.S. patent application Ser. No. 12/243,404, filed on Oct. 1, 2008, entitled "Systems and Methods for Aiding Computing Users Having Sub-Optimal Ability", which claims priority from U.S. Provisional Patent Application No. 60/997,168, filed on Oct. 1, 2007, entitled "Systems and Methods for Instruction and Aid of Aging Computer Users," all of which are incorporated herein by reference in their entireties.

BACKGROUND OF THE INVENTION

1. Field of the Invention

This invention relates, generally, to computer-implemented educational tools. More particularly, it relates to an educational tool and use thereof for social benefit and increased cognitive wellness in a variety of users, for example sufferers of dementia.

2. Description of the Prior Art

Cognitive wellness in all human beings is affected by a plethora of internal and external factors, including age, intelligence, culture, stress levels, anxiety, nutrition, and medication, among others. In turn, cognitive wellness itself can affect social capacities, performance on various tests, and basic abilities to function on a daily basis, among others. Therefore, persons with lower cognitive wellness might have lower test scores or difficulties performing basic tasks.

These difficulties are further exacerbated in individuals having diminished or declining physical (i.e., neurophysiological) or mental (i.e., cognitive or logic) capacities. Individuals prone to these diminished or declining physical or mental capacities can include the elderly, mentally handicapped individuals, and those who have suffered debilitating injury or disease. These individuals are particularly prone to depression and anxiety brought on by feelings of helplessness and isolation caused by a decline in physical or mental capacities.

For example, in elderly persons with dementia, conventional memory aids and drugs are used for treatment. Various memory aids are known but are not sufficiently personalized to each person to provide that person with daily relief and comfort in social settings. Drugs, such as cholinesterase inhibitors, used in treatment of dementia, merely treat the symptoms rather than the underlying root of the symptoms and cannot be the sole treatment method of dementia. Moreover, drugs are invasive and tend to have enhanced side effects in the elderly. These side effects, including chemical imbalances in the body, can hinder a patient's independence and comfort in contacting his/her social network (i.e., due to memory problems, agitation, nausea, etc.), thereby also enhancing feelings of hopelessness.

Accordingly, what is needed is an improved system and method for maintaining or increasing cognitive wellness, particularly to enhance memory recollection. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved, more effective and non-invasive system and method for enhancing social memory recollection is now met by a new, useful and nonobvious invention.

An embodiment of the current invention is a computer-implemented software application for goal-oriented, personalized memory recollection training The software includes instructions for initially receiving a personal goal of a user and determining the user's capacities for learning and memory based on the user's responses given in one or more baseline tests administered to the user. These capacities allow the software to determine the user's baseline cognitive ability, which communicates expectations and assumptions of the user's cognitive abilities as the user progresses through memory training. Based on the user's personal goal and baseline cognitive ability, the software automatically generates a cognitive test containing variable parameters and administers the cognitive test to the user. The user's tested cognitive ability is then determined based the user's responses in the cognitive test. The user's tested cognitive ability is then compared to the user's baseline cognitive test. If the tested cognitive ability meets the expectations (i.e., expectation range) and assumptions of the baseline cognitive ability, then the cognitive test may be automatically generated and administered again or as modified. If the tested cognitive ability fails to meet or exceeds the expectations and assumptions of the baseline cognitive ability, then the baseline tests are automatically administered to the user to re-determine/correct the user's baseline cognitive ability, followed by re-generating the cognitive test according to the user's personal goal and updated baseline cognitive ability.

The user's personal goal may also be modified if the user's tested cognitive ability fails to meet the expectations and assumptions of the user's baseline cognitive ability, followed by re-generating the cognitive test according to the user's personal goal and updated baseline cognitive ability.

More than one cognitive test may be administered to the user prior to determining the user's tested cognitive ability. Each cognitive test can have different testing parameters to test the user in different situations. Having a larger sample size of cognitive tests may allow for a more accurate tested cognitive ability to be determined.

The software can determine the user's capacity for gain when more than one baseline tests are administered. In this case, the software's determination of the user's baseline cognitive ability would be further based on the user's capacity for gain.

The one or more baseline tests initially administered to the user may include two series within one baseline testing session. The first series is administered to the user and includes one or more training methods from the group consisting of free recall, graduated cuing, vanishing cuing, and spaced retrieval. Subsequently, the second series is administered to the user and is substantially similar to the first series. The user's capacity for learning is, therefore, determined by comparing the user's performance from the first series to the second series. Each baseline test is personalized to the user and created via a unique combination of memory test techniques and performance parameters.

The one or more baseline tests may be administered periodically to the user, so the user's baseline cognitive ability can be updated over time.

If the user consistently identifies targets correctly, the software may automatically modify the testing parameters of the cognitive test to be more difficult in real-time. If the user consistently identifies targets incorrectly, the software may automatically modify the testing parameters of the cognitive test to be less difficult in real-time. The user's personal goal can be modified accordingly as well to be easier or more difficult to achieve.

A separate embodiment of the current invention is a computer-implemented method of providing personalized memory recollection training to a user having suboptimal cognitive acuity. The method includes receiving and storing data associated with a plurality of members of the user's social network. The user is administered a first baseline memory test. If the user failed the first baseline test, then the user is administered a second baseline memory test. Thereafter, the method includes determining the user's baseline cognitive ability based on the results of the first and second baseline memory tests. The user is then administered a memory training exercise, which has a difficulty automatically determined by the user's baseline cognitive ability. The training content is based on the data of the user's social network, so the user may achieve socially-oriented goals, for example being able to identify a neighbor.

The data may include a name and a photograph of a member of the user's social network. Alternatively, the data may include a separate prompt and target in any field of memory for achieving a goal, such as recalling objects or actions.

The data may be stored in a computer-readable data store, and the user's access to the data may be limited by the baseline cognitive ability of the user.

The first baseline memory test may be a free recall test. In a further embodiment, the second baseline memory test can be a graduated cuing test, vanishing cues test or spaced retrieval test. The type of second baseline memory test is automatically determined based on the user's results of the first baseline memory test.

The user's baseline cognitive ability may be automatically adjusted based on the user's performance in the memory training exercise.

The memory training exercise may be administered periodically to the user.

A separate embodiment of the current invention is a computer-implemented method of sending a text-based, image-based, video-based or audio-based message. An authorized party submits a preferred method of communication for each of a plurality of contacts in a user's address book or directory. The preferred method of communication has a first set of allowable message parameters. The user can compose a message by first selected a recipient from the plurality of contacts. Upon composing the message, it is determined whether the message meets the first set of allowable message parameters. If it meets the parameters, the message is sent via the preferred method of communication. If the message does not meet the parameters, the message is sent via an alternate method of communication that has a second set of allowable message parameters that conform to the message.

The preferred method of communication may be email, text message, social network post, social information message, video message, voice message or instant message.

The plurality of contacts of a user may be defined by administering a series of baseline cognitive tests and memory training A test algorithm utilizes the results of the baseline tests and memory training to personalize the display or content of the plurality of contacts for the user.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

In certain embodiment, the memory recollection training system ("MRTS") is an apparatus and a method of increasing or maintaining users' cognitive wellness while providing social benefits to users as well. It is a system that can be used by a variety of users with wide ranges of cognitive abilities. In one embodiment, a student may use it as a study aid. In another embodiment, an elderly person with diminished mental capacity may use it to cope with daily life.

The MRTS gathers and organizes sets of information inputted by authorized parties. The information can then be used in a variety of ways and forms, from games to subject lessons to face-name training Additionally, the MRTS may provide a medium of communication. If an individual's information, such as names and contact information are inputted, the MRTS may use this information to allow users to communicate with those individuals more easily.

The MRTS may provide an interface layer through which communications to users can be normalized by making consistent the values reads (e.g., format) of the communications. The information inputted into the MRTS can be used in each aspect of the MRTS to personalize the user's experience. Also, when the MRTS receives information/signals from the user himself/herself (e.g., time it takes to answer a question, frequency of use, etc.), the MRTS can adapt the user's experience to the user's cognitive wellness.

Inputting Information into MRTS

A set of information is created and inputted by authorized members of the user's social network. In an embodiment, the set of information may include an individual's name, picture, relationship to user, phone number(s), cell phone provider, email address, mailing address, social information (e.g., FACEBOOK, TWITTER, SKYPE, FLICKR, YOUTUBE), interests, education, and/or other pieces of information about the individual or contact methods to the individual. Further or alternatively, the set of information may include various objects, actions, topics or subject areas that a user may wish to have the ability to recall or on which a user might be tested. Authorized members of the user's social network include, but are not limited to, the user, friends, family, educators, staff members implementing MRTS, assisted living facility staff, other residents in an assisted living facility and/or other authorized parties. The set of information may also be pulled from a localized resident management system or other database to which the user's MRTS is connected.

Figure 2:
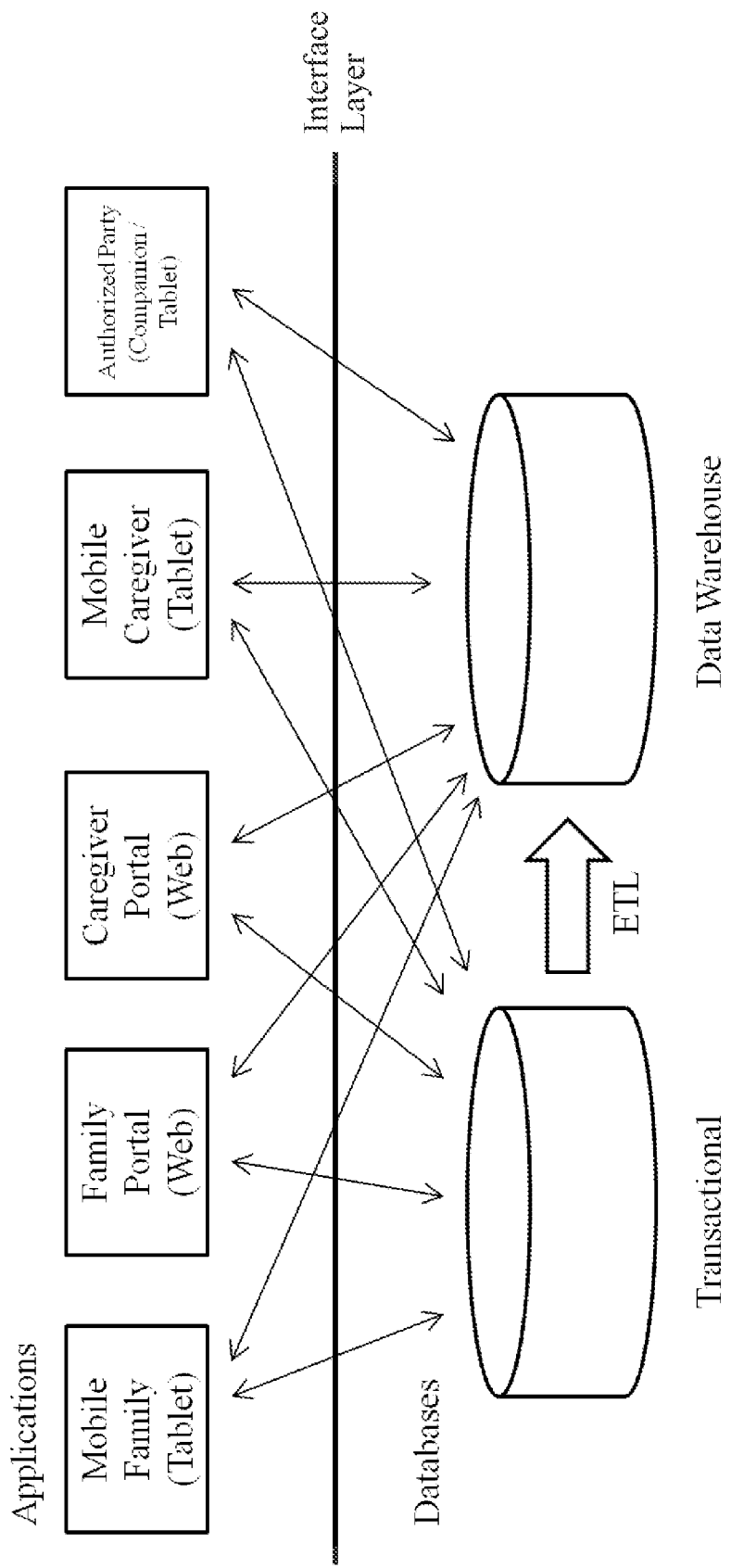
FIG. 2 depicts an example of the process of a set of information being inputted into a memory recollection training system through a variety of intakes.

Examples of inputting the set of information are depicted in FIG. 2. In an embodiment, an access- or login-based application may be used by authorized members of the user's social network to input this set of information into a transactional database. In another embodiment, the user's authorized family members or caregivers may access the Internet to input this set of information. In another embodiment, authorized members of the user's social network may access a web-based application to input this set of information into a transactional database. In another embodiment, authorized mobile family or caregivers may access an application on a tablet computer to input this information into a transactional database. In another embodiment, a SIMPLEC Companion or application on a tablet computer may be used by SOCIALC (i.e., a normalized, integrative contact application presented to the user) to input this set of information into a transactional database. In another embodiment, authorized members of the user's social network may access a web-based application to input this set of information into a data warehouse. In another embodiment, authorized mobile family caregivers may access an application on a tablet computer to input this information into a data warehouse. In another embodiment, a SIMPLEC Companion or application on a tablet computer may be used by SOCIALC (i.e., a normalized, integrative contact application presented to the user) to input this set of information into a data warehouse. Other input methods known in the art are contemplated as well.

In any embodiment wherein a data warehouse is used subsequent to a transactional database, the set of information may be transferred from the transactional database to the data warehouse by extracting, transforming and loading the data into the data warehouse, or other transfer method known in the art. The set of information may be inputted one or more times, or may be deleted or modified in the database. The set of information, when inputted, may pass through an interface layer controlled by staff members (e.g., from SIMPLEC) implementing MRTS or another authorized party. This interface layer normalizes communications to media, thereby allowing all value reads of the set of information to become consistent with each other, in turn allowing output of information to be standardized. This output can be used in a variety of ways, for example personalizing exercise portals, communications with a social network, and computer use.

Directory of MRTS

Figure 1:
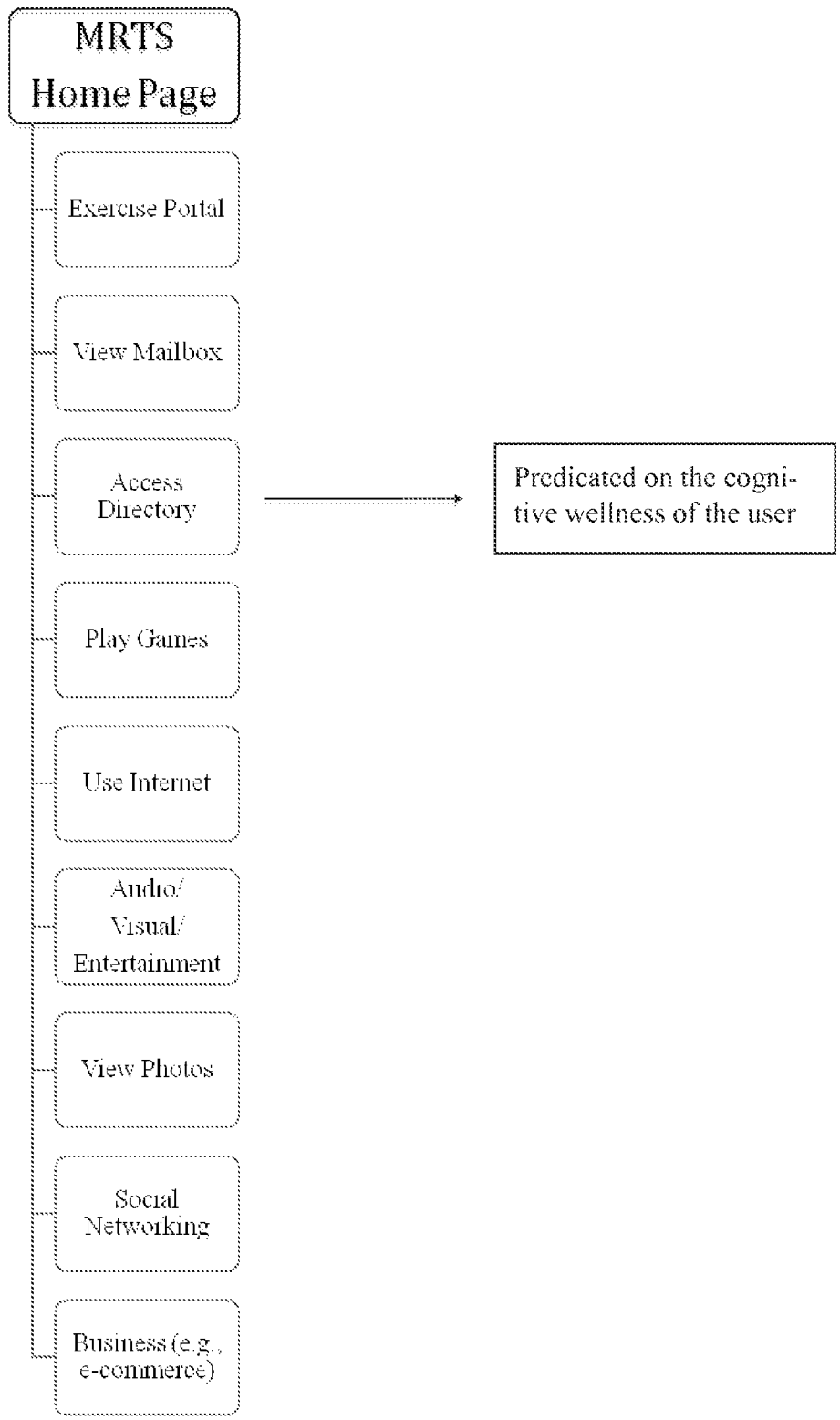
FIG. 1 depicts an example of a homepage of a memory recollection training system.

After being inputted, the set of information feeds into a Directory, which collects, organizes and stores the set of information. The Directory then feeds into various applications on the homepage of MRTS, for example as depicted in FIG. 1. The homepage may include options to select an Exercise Portal, View Mailbox, Directory, Games, Internet Browser, online entertainment, Photos, business, and/or other useful applications. The exercise portal reinforces the mailbox, or intelligent uniform inbox. For example, based on a user's performance in the exercise portal, a particular photograph of a contact in the Directory may be selected by the system to be displayed to the user. A user's access to the Directory, as depicted in FIG. 1, may be predicated on the user's level of cognitive wellness. If the user has mild cognitive impairment or higher cognitive ability, the user may have access to the Directory. If the user has mild cognitive impairment to severe cognitive impairment, then the user may have limited or no access to the Directory. Limited access can include the ability to only read the Directory, read and write within the Directory, requirement of supervision or authorization to edit the Directory, etc. Access to the Directory includes the ability to add, delete or modify contacts therein.

Games

The Directory may feed into the MRTS' Games section, whereby the set of information can be used within the Games to personalize the Games for each user.

Exercise Portal

The Directory may feed into an exercise portal. The exercise portal is a tool used to measure cognitive state, and track and record changes in cognitive health over time. For example, a more specific goal may be to engage a user (e.g., resident in assisted living facility) and teach the user memory-based tasks, such as remembering names of the individuals in the user's social network. It is a series of baseline tests, recurring tests, learning activities and practices. The goal of the exercise portal is to reinforce the association between two or more stimuli. The stimulus that is given to the user is the prompt, and the stimulus that is the object of identification is the target. Examples of prompt-and-target pairings include, but are not limited to, a face (image prompt) and a name (word target), an object (image prompt) and a name (word target), a question (word prompt) and an answer (word target), and a sound (auditory prompt) and an identification (word target). Though each target is shown as a word target, a target can also be an extraction of a word, such as a user speaking the word through voice or communicating the word through sign language. Each pairing is an item. Using the example of a face-name item, the goal is to use face-name training methods to stimulate free recall in anyone wishing to maintain or increase cognitive wellness/abilities.

Any training methods may be used in the tests, learning activities, and practices of the exercise portal. Examples include, but are not limited to, free recall, graduated cuing, vanishing cues, and spaced retrieval. Particular training methods (e.g., graduated cuing, vanishing cues, spaced retrieval) include cues, or an intermediary stage between a prompt and a target for aiding a user in the proper identification of the target. The training methods can be administered or used individually or in combination.

In the free recall method, a user is asked a question after being shown a prompt or asked a question about a prompt or stimulus. The free recall method generally does not involve memory cues, as the ultimate goal of many of these training methods is to enhance free recall in the user.

In the graduated cuing method, the first step is the acquisition phase, wherein a prompt, a target, and/or other value from the set of information are displayed to the user. All information (primarily the target), except one piece of information (primarily the prompt) subsequently disappears. The user can then be asked to identify the target. If the user is correct, a "Successful" or equivalent screen may appear. If the user is incorrect or cannot remember, a cue is provided. Using graduated cuing, "n" number of letters of the target may appear, where "n" can vary as any integer. The user might be asked again for the target. The process of "n" letters appearing repeats until the user correctly identifies the target without cueing (i.e., free recall has been established).

In the vanishing cues method, the first step is the acquisition phase, wherein a prompt, a target, and/or other value from the set of information are displayed to the user. All information (primarily the target), except one piece of information (primarily the prompt) subsequently disappears. The user can be asked for the target to the question. If the user is correct, "n" letters of the target are withdrawn. The user can then be asked again for the target. The process of "n" letters vanishing repeats until the user correctly identifies the target while being provided zero letters of the target (i.e., only the question/picture is shown). If the user identifies the target incorrectly or cannot remember, a cue can be provided, for example in the form "n" letters of the target reappearing. The process of "n" letters of the target reappearing repeats until the user correctly identifies the target. When the user correctly identifies the target, the process of "n" letters vanishing may restart.

In the spaced retrieval method, the first step is the acquisition phase wherein a prompt, a target, and/or other value from the set of information are displayed to the user for "x" amount of time, where "x" can be any amount of time. After "x" time, all of the displayed information may disappear. Thereafter, cues describing or illustrating the target or another prompt, task or item may appear for a period of time (e.g., "y" time). Any cue or prompt from the acquisition phase can reappear, as the user is asked to identify the target.

Alternatively, rather than all of the displayed information disappearing, only the target may disappear, leaving the prompt and/or some cues. The user may then be asked to identify the target. If the user is correct, the process of the information disappearing and reappearing after a period of time repeats with increasing time intervals for the information disappearing phase. The general goal is for the user to be able to identify the target after longer periods of time. If the user incorrectly identifies a target, one option is a graduated cuing method beginning with "n" letters of the target appearing. The process of "n" letters appearing repeats until the user correctly identifies the target. When the user correctly identifies the target, the initial spaced retrieval method (i.e., process of the information disappearing and reappearing after increasing periods of time) may restart. A second option is for the time interval between information appearing and disappearing to decrease (e.g., z") until the user correctly identifies the target. When the user correctly identifies the target, the initial spaced retrieval method (i.e., process of the information disappearing and reappearing after an increasing period of time) may restart.

Personalization Based on Information—Regular Patterns

The goal of these, and other, training methods is to increase free recall of a target when provided a prompt. The set of information inputted into the Directory is outputted uniquely in the training methods to enhance free recall of the set of information. This use of the user-specific set of information allows for complete personalization to the user resulting in goal-oriented social benefits for each specific user.

The pattern of testing (e.g., graduate cues, vanishing cues, spaced retrieval) would be presented to the user in regular patterns previously set by authorized members based on the baseline cognitive ability of the user (i.e., manual) or determined by the test algorithm (i.e., automated). In other words, "n" letters in the graduating and vanishing cues methods may remain constant or occur in regular patterns, or "x" time intervals in the spaced retrieval method may remain constant or occur in regular patterns.

Personalization Based on Algorithm—Personalized Patterns

In certain embodiments, the MRTS uses a unique algorithm to adapt or personalize training patterns to each user, rather than administering the training in regular patterns. A user goal is defined and inputted into the algorithm. Examples of specific goals may include ability to remember targets immediately, ability to remember placement of keys for a 24-hour period, etc. The user is administered one or more baseline tests with a plurality of variable criteria, and based on the user's results of the baseline tests, the algorithm will map/calculate the user's current capacity for learning, capacity for memory, capacity for gain, accuracy of recall (i.e., whether the user remembered/identified the target correctly), and capacity for reaction time (i.e., time needed for the user to identify the target. Learning is the ability for a user to freely recall targets within one testing session (i.e., over a shorter term period). For example, learning can be indicated by retention levels from a couple seconds up to twenty minutes or longer, depending on the user's goal. Memory is the ability for a user to freely recall targets between testing sessions (i.e., over a longer term period). For example, memory can be indicated by any retention levels beyond one training session, such as an hour, a day, a week, a month or longer, depending on the user's goal. Gain is the user's speed of learning over time. In a typical healthy user, the user's capacity for gain is higher initially since the user can learn a lot and gradually declines as the user approached his/her maximum potential. Reaction time is the time needed for the user to correctly identify the target upon being provided a prompt and/or hint/cue. Based on these capacities, the algorithm can determine the user's baseline cognitive ability, which measures how cognitively able a user is prior to undergoing initial or further memory recollection training.

In an embodiment, the baseline tests may include a series of free recall tests, which determines whether a user can identify targets based on another value from the set of information without use of any cues. If the user is consistently successful, the user may be considered highly cognitive, and the algorithm automatically determines what training is needed and how the application will be displayed. Based on the percentage correct of correct target identifications, the user is automatically directed to the appropriate training and display. If the user is consistently unsuccessful with the free recall test, the application may automatically direct the user to a graduated cuing test, as previously described. If the application determines that the user is successful in the graduated cuing test, the application may automatically direct the user to a spaced retrieval test. Alternatively, if the application determines that the user is unsuccessful in the graduated cuing test, the application may automatically direct the user to a vanishing cues test. The general idea is that free recall is the most difficult test, followed by spaced retrieval, graduated cuing, and vanishing cues. However, this order of difficulty can be adjusted since a plurality of parameters within each test can be changed to be easier or difficult.

Alternatively, a baseline test can include a plurality of types of testing, and the user's results of each type of testing can be triangulated by the application to determine the user's baseline cognitive ability. The types of testing administered in this baseline test can be random or pre-planned based on any preconceived notion of the user's cognitive state.

Through each test, the application can measure the correct and incorrect answers, amount of time needed to reach those answers, and/or any other measurable factors affecting a user's answers in each test. The algorithm can determine how many cues to provide, how much information to use in training or to allow into the Directory of the MRTS, how many cues to give per question, what kind of cues to give, how much time to allow for answers, the time intervals in the spaced retrieval therapy, and/or any other variable that can be adjusted within the training and affect the user's identification of answers.

Adaptability

Features of the MRTS may change or turn on or off as a user's cognitive abilities are influenced through use of the exercise portal and other factors (e.g., increased age, etc.). The MRTS can gather data from the user's communication (e.g., frequency of communication) and other actions within the application to determine which features should be added, deleted, or modified. For example, access to the Directory may turn off when the application determines that the cognitive wellness of the user has declined past a certain threshold. As another example, the features or cues described in the training exercises of the exercise portal can be altered based on measurements of the user's cognitive ability. Measurements are taken from the user's identification of answers in the training tests, and factors thereof (e.g., time taken to identify answer, correct or incorrect answer, etc.). If the set of information in a user's Directory includes identification of various people in the user's social network, the people may administer tests to measure the cognitive abilities of the user. The MRTS also allows the user to learn and practice the user's cognitive abilities and stimulate the neurons to increased levels of free recall and communication, thereby providing all relevant parties knowledge of expectations and a better quality of life. An object of the MRTS is to enhance, improve, maintain or reinforce quantity and quality of communication of the user to individuals in the user's social network. By utilizing the MRTS, the user may feel more comfortable communicating with others.

Example 1

An embodiment of the MRTS includes an educational tool for elderly users to recognize/identify and communicate with their individual social networks (e.g., friends, family, caregivers, other persons) more effectively.

The Directory provides a personalized list of people whose profile the user may want to view or follow. The Directory is used to view Photos of the persons whose set of information has been inputted into the Directory. The Directory is also used to create a contact list for making phone calls, for example through Voice over Internet Protocol. The Directory is also used when the user logs onto a social networking website (e.g., FACEBOOK, MYSPACE, TWITTER, FLICKR, YOUTUBE, etc.).

The Directory feeds into an exercise portal. The exercise portal is a tool used to measure cognitive state, teach users memory tasks, and track and record changes in cognitive wellness over time. It is a series of baseline tests, recurring tests, learning activities and practices. The goal of the exercise portal is to use face-name training to stimulate free recall in elderly users wishing to maintain or increase cognitive wellness as their cognitive wellness naturally decreases over time.

Figure 4:
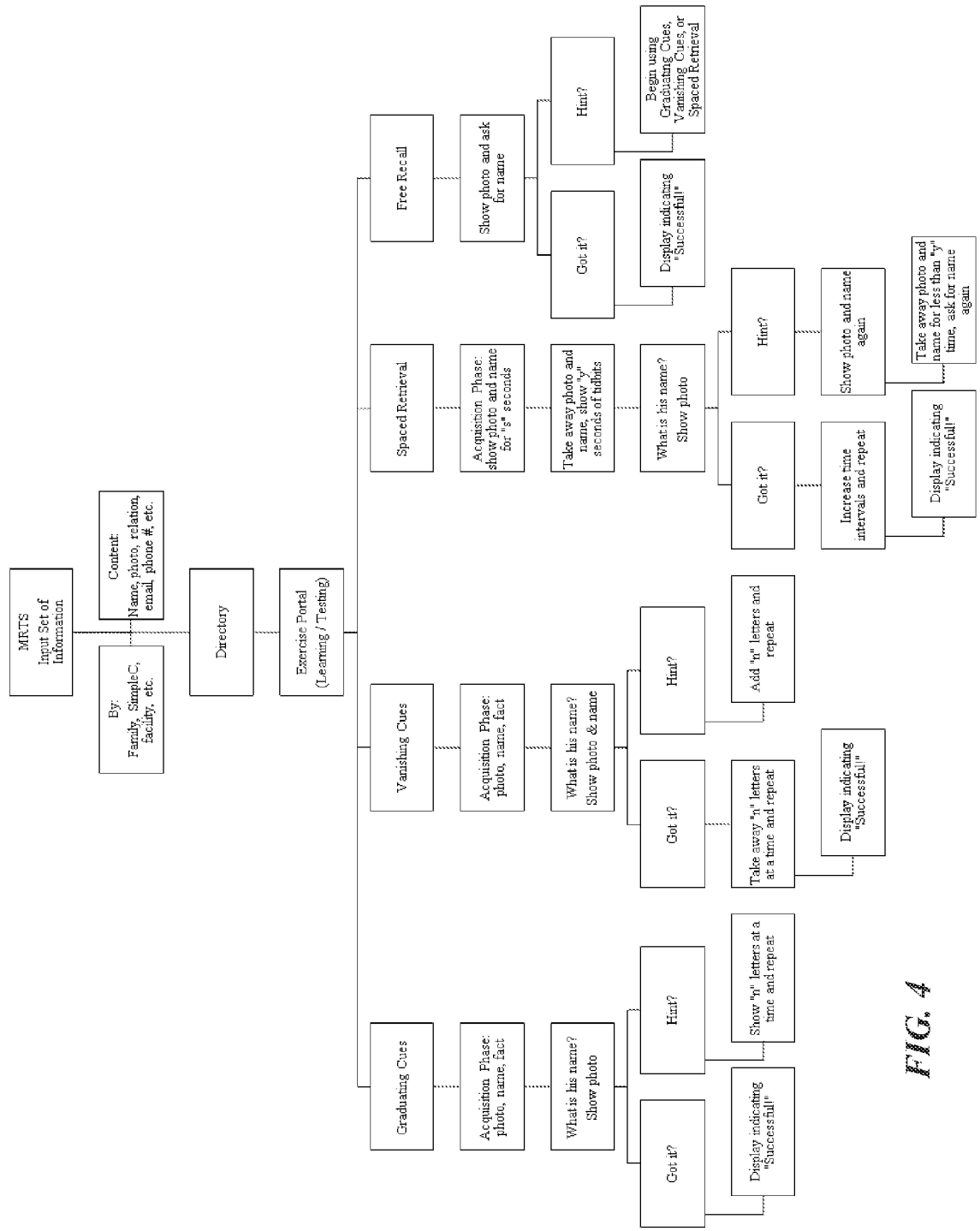
FIG. 4 depicts an example of an exercise portal utilized via a memory recollection training system.

As depicted in FIG. 4, the exercise portal includes at least four methods of face-name training in its tests, learning activities and practices. These four methods are free recall, graduated cuing, vanishing cues and spaced retrieval. The training methods can be used either individually or in combination, as described herein.

In the free recall method, a user is asked to identify the name of an individual from the Directory after being shown one or more of the individual's photos, facts, videos, audio clips, or other type of media.

In the graduated cuing method, the first step is the acquisition phase, where an individual's name, photo, fact, and/or other value from the set of information is displayed. All information (primarily the individual's name), except one or more pieces of information (e.g., individual's photo), subsequently disappears. The user is then asked to identify the individual by name. If the user is correct, a "Successful" or equivalent screen is displayed. If the user is incorrect or cannot remember, "n" letters of the individual's name appears. The user is then asked again for the individual's name. The process of "n" letters appearing repeats until the user correctly identifies the individual's photo/fact with that individual's name.

In the vanishing cues method, the first step is the acquisition phase, where an individual's name, photo, fact, and/or other value from the set of information is displayed. All information, except the individual's photo/fact and name, subsequently disappears. The user is asked to identify the individual's name. If the user is correct, "n" letters vanish or disappear from display. The user is then asked again to identify the individual's name. The process "n" letters vanishing repeats until the user correctly identifies the individual's photo/fact with that individual's name while being provided zero letters of the individual's name (i.e., only the individual's photo/fact shown). If the user provides an incorrect identification or cannot remember "n" letters of the individual's name may reappear. The process of "n" letters of the individual's name reappearing repeats until the user correctly identifies the individual. When the user correctly identifies the individual, the process of "n" letters vanishing may restart.

In the spaced retrieval method, the first step is the acquisition phase, where an individual's name, photo, fact, and/or other value from the set of information is displayed for "x" time. After "x" time, all of the displayed information may disappear. Thereafter, tidbits of facts describing the individual may appear for a period of time (e.g., "y" time). One or more pieces of information from the acquisition phase, except for the individual's name, may reappear. The user is then asked to identify the individual by name. If the user is correct, the process of the individual's information disappearing and reappearing after a period of time repeats with increasing time intervals for the information disappearing. If the user is incorrect identifying the individual, one option is a graduated cuing method automatically beginning with "n" letters of the individual's name appearing. The process of "n" letters appearing repeats until the user correctly identifies the individual. When the user correctly identifies the individual, the initial spaced retrieval method (i.e., process of the individual's information disappearing and reappearing after an increasing period of time) may restart. A second option is for the time interval between an individual's information appearing and disappearing to decrease (e.g., "z") until the user correctly identifies the individual. When the user correctly identifies the individual, the initial spaced retrieval method (i.e., process of the individual's information disappearing and reappearing after an increasing period of time) may restart.

The goal of these training methods is to increase free recall of names of individuals in a user's social network. The set of information (i.e., names, photos, facts, etc.) inputted into the Directory is outputted uniquely in the training methods to enhance free recall of the set of information. This use of the user-specific set of information allows for complete personalization to the user resulting in social benefits for each specific user.

The pattern of testing (e.g., graduate cues, vanishing cues, spaced retrieval) would be presented to the user in regular patterns previously set by authorized members. In other words, "n" letters in the graduating and vanishing cues methods may remain constant or occur in regular patterns, or "x" time intervals in the spaced retrieval method may remain constant or occur in regular patterns.

However, if more personalized patterns are desired, the MRTS includes an algorithm that further personalizes each training method to each user by determining all aspects of each training session, for example including, but not limited to, number of images of individuals used in training, number of individuals used in training or allowed onto the application, number of facts used per photo or per individual, category of facts used in training (e.g., name, interests, education, hometown, etc.), amount of time allowed for answers, extent of time intervals in spaced retrieval therapy, and/or any other variable that can be adjusted within the training and affects a user's identification of answers within the training.

Figure 3:
FIG. 3 depicts an example of the process by which a message may be received or sent through a memory recollection training system.

As depicted in FIG. 3, the Directory also feeds into and creates an Address Book. The Address Book contains one or more values from the set of information previously inputted and may be viewed on one or more displays. In a user's Mailbox, the user can view a message sent by contacts in the user's Address Book without specifically having to access the user's email system, text messages, social networking websites, etc., similar to the universal inbox disclosed in U.S. Pat. No. 6,430,174 to Jennings, which is hereby incorporated by reference. A message may include text, pictures, videos, voice, and/or other method of text-, audio-, video-, or image-based communication. The source of the message is transparent to the user. Messages from the user's social network will appear chronologically to the user automatically in a normalized format, so the user does not feel confusion or anxiety having to take extra steps to view and respond to messages. The term "normalized format" is used herein to refer to a uniform presentation display for the user. Therefore, whereas conventional universal inboxes simply gather messages in one location (i.e., the messages still appear in different formats), in the current invention messages from a plurality of different sources appear in one standard format.

Additionally, if the user wishes to send a message to a contact in the user's Address Book, the user does not need to choose a method of sending the message. Rather, contacts in the user's social network will have preselected a contact method preference when their set of information was inputted. Therefore, when the user wants to send a message to a contact, the user simply has to choose to send a message to the contact. The message is composed and sent automatically in the preferred method that the contact preselected. If the user's message does not conform to the contact method preference, for example the message being over 140 characters if the contact method preference is TWITTER, then the system will automatically choose the best method of sending the message based on format and/or content or an alternate method preselected by the recipient. Alternatively, in another example, if the preferred method of communication is a phone call or voice message and the user begins typing on a computer, then system will automatically choose the best text-based method of transmitting the message.

Optionally, the system can use the user's results from baseline testing and memory/cognitive training to define and personalize the content or display of the user's contacts to the user. For example, if a user has consistently identified a contact correctly based on the contact's photo, as seen in the baseline testing and training, then the system can automatically reinforce the contact in the Address Book by displaying the contact's photo only when sending or receiving a message.

Example 2

Figure 6:
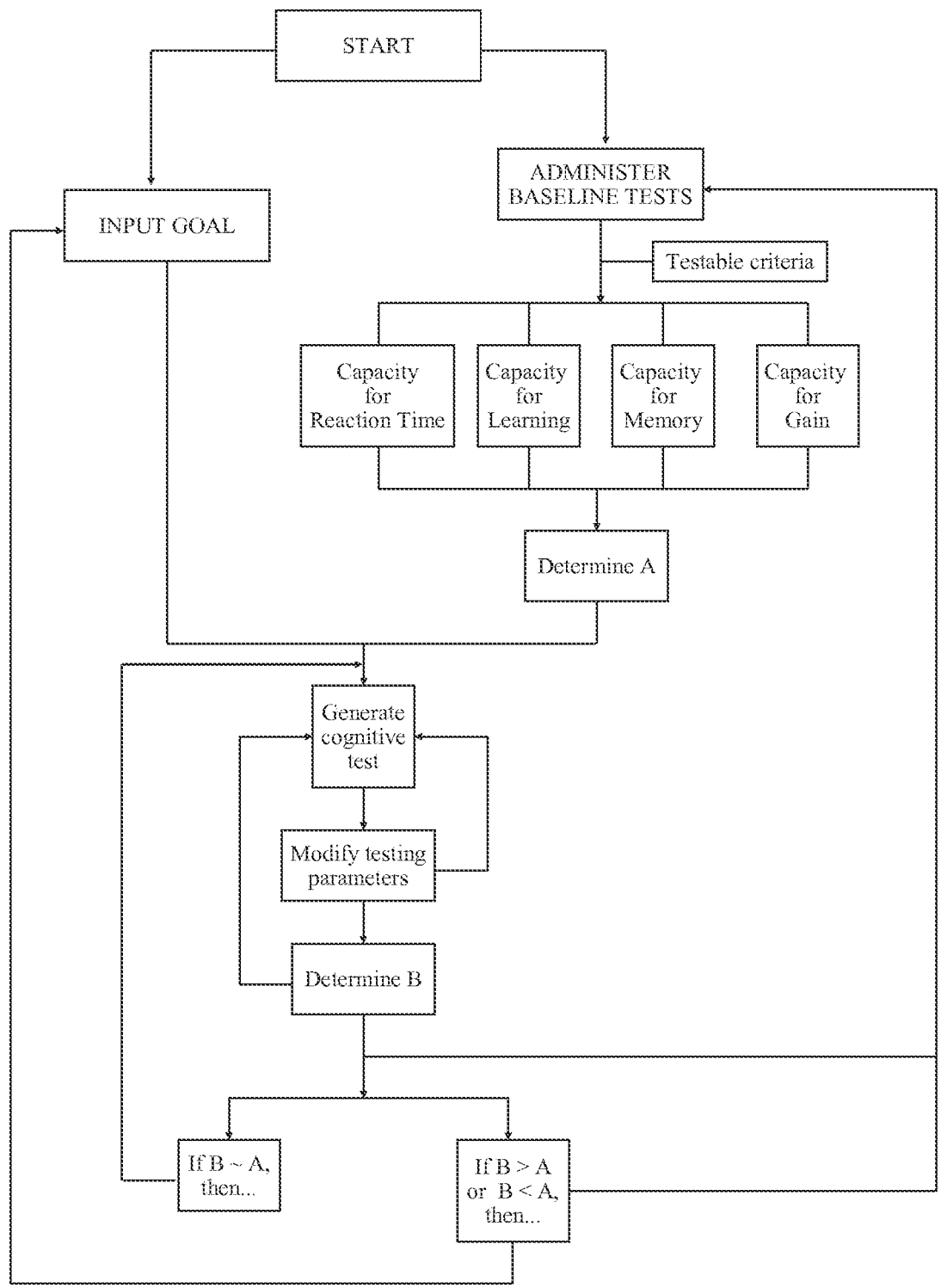
FIG. 6 depicts a step-by-step flow chart illustrating an algorithm used in a memory recollection training system.

As depicted in FIG. 6, a user goal is defined and inputted into the algorithm. Examples of specific goals may include ability to remember targets immediately, ability to remember placement of keys for a 24-hour period, etc. The user is administered one or more baseline tests with a plurality of variable criteria, and based on the user's results of the baseline tests, the algorithm can map/calculate the user's capacity for learning, capacity for memory, capacity for gain, and capacity for reaction time. Learning is the ability for a user to freely recall targets within one testing session (i.e., over a shorter term period). For example, learning can be indicated by retention levels from a couple seconds up to twenty minutes or longer, depending on the user's goal. Memory is the ability for a user to freely recall targets between testing sessions (i.e., over a longer term period). For example, memory can be indicated by any retention levels beyond one training session, such as an hour, a day, a week, a month or longer, depending on the user's goal. Gain is the user's speed of learning within and between training sessions. Reaction time is the amount of time needed for a user to correctly identify a target when given a prompt and/or hint. Based on these capacities, the algorithm can determine the user's A, or baseline cognitive ability, which measures how cognitively able a user is prior to undergoing initial or further memory recollection training.

Baseline tests are given to assess the user's ability to learn, remember and correctly identify targets based on prompts with support from cues. The baseline tests are a combination of the free recall method and graduated cuing method, though any combination of training methods is contemplated. A series of items (e.g., fifteen items) are presented to the user. If the user correctly identifies the target of the item when only the prompt is provided, the next item is presented. If the user incorrectly identifies the target, the prompt and the target are presented together ("repeat"), and the user is asked to identify the target. The user can be given positive reinforcement, as the goal in this case is for the user to identify the target whether the target is displayed or not. Once this first series of items are presented and complete, the test is repeated using the same series of items a second time ("second series"). The difference in performance between the first and second series indicates the user's learning.

In a single test, the algorithm dictating the baseline test automatically establishes an initial memory score (i.e., how many targets the user could identify correctly in the first series of the test) and an initial learning score (i.e., how many targets the user could correctly identify in the second series of the test compared to the first series). As the baseline test is given multiple times over a time period, preferably four or more times wherein the baseline test remains constant, changes in memory or cognitive ability can be measured by comparing results between baseline tests. The difference in performance between baseline tests indicates the user's memory. Additionally, the user's capacity for gain (i.e., the speed at which the user learns and develops memory) can be determined by the algorithm over the period of time. The user's accuracy (i.e., whether the target was identified correctly) and reaction time (i.e., how quickly the target was identified) can be measured and monitored to calculate the user's capacities for learning, memory, gain, and reaction time. Goals for reaction time are dependent on personal goal of each user. For example, if the user's personal goal is to remember placement of keys, reaction time might be optimized at remembering placement of keys for 24 hours. If the user's personal goal is to remember a neighbor's name, reaction time might be optimized at recalling the name immediately.

Scoring of the baseline tests can be performed in a variety of ways by the algorithm to automatically determine the user's capacities and baseline cognitive ability. Baseline scoring can be performed by measuring the percent correct in the first series of items, percent correct in the second series of items, reaction time in the first series, reaction time in the first series, reaction time in the second series, total completion time in the first series, and total completion time in the second series. The algorithm also tracks consistent successes, for example by item, subject (i.e., identities of persons in social network, placement of keys, etc.), time of day (i.e., whether the user performs better in the morning, afternoon or evening), target, duration of exposure of each prompt, duration of exposure of each target, retention rate between repeats (when user has incorrectly identified the target), and retention rate between the first series and the second series. The algorithm also tracks consistent failures, for example by item, subject, time of day, target, duration of exposure of each prompt, duration of exposure of each target, retention rate between repeats (when user has incorrectly identified the target), and retention rate between the first series and the second series. The algorithm also measures the percent of correct target identifications between repeats, between series, in the first series individually, and in the second series individually. The algorithm also measures change in time to respond to each prompt between the first and second series, in the first series individually, and in the second series individually. The algorithm also measures total time between the first and second series, in the first series individually, and in the second series individually. The algorithm uses some or all of the foregoing measurements to automatically create the user's unique capacities for memory, learning, gain, and reaction time. These capacities are plotted against testable criteria (e.g., correct answers, reaction time, etc.), and their graphical characteristics (e.g., slope, maximum level, shape of curve, etc.) are determined to automatically create the user's personal baseline cognitive ability, which is an overall assessment of the user's maximum potential and variation thereof.

In a preferred embodiment, the main measurement of interest is a performance parameter or percent of correct identifications. Reaction time is a parameter or function of a user's personal disposition (i.e., the user's processing speed, motor skills, language capabilities, etc.), learning capacity and memory capacity. Reaction time affects the learning and memory capacities, and also is affected by the user's learning and memory capacities. Gain is a reflection of the user's capacities for learning and memory.

Still referring to FIG. 6, the MRTS algorithm utilizes the user's personal goal and baseline cognitive ability to automatically create cognitive testing/training methods, including, but not limited to, test type (e.g., free recall, spaced retrieval, graduated cues, vanishing cues), number of items in the test, number of stimuli shown (e.g., add or remove a last name from a full name target), stimulus exposure time (e.g., showing prompt for more or less time), and varying the individual parameters of the test type (e.g., interval time during spaced retrieval, number of letters added during graduated cuing, number of letters removed during vanishing cues, percentage of target added, shown or removed, etc.).

Generally, a goal of the baseline testing is to assess capacity of the user or set the overall expectation for the user (e.g., how many identifications the user can be expected to have correct). A goal of the cognitive testing is to train the user to capacity (i.e., success relative to the user) or achieve the user's personal goal (e.g., lowering the user's reaction time for social benefit). Cognitive testing includes cues, and the extent of cuing necessary for the user to correctly identify the target varies and reflects the strength of the user's memory trace. If the user's memory trace is weaker, more effort and assistance (i.e., cuing) is required.

In free recall training, the MRTS provides the user with a prompt and asks the user for the target with no cue. If the user correctly identifies the target, the next prompt is provided. If the user incorrectly identifies the target, the target is displayed with the prompt. When the user correctly identifies the target, the user is given positive reinforcement, and the next prompt is provided. The goal of reaction time is to trend toward zero or immediate target identification (minimum) or the maximum capacity established in baseline testing. The goal of accuracy is to trend toward 100% (maximum) or the maximum capacity established in baseline testing.

In spaced retrieval training, the MRTS provides the user with a prompt and target together until the prompt and target are both removed for a period of time ("wait period"). The prompt is subsequently provided to the user, and the user is asked to identify the target without cues. If the user correctly identifies the target, then the MRTS automatically re-administers the test with an increased wait period to determine the extent of the user's retention ability. If the user incorrectly identifies the target, then the MRTS automatically re-administers the test with a decreased wait period to determine the extent of the user's retention ability. If the test is iterating over a single item, then the MRTS continues to administer the test until a correct answer is given after a particular wait period, or until the user provides a particular number of incorrect answers at a constant wait period, or until the user provides a particular total number of wrong answers. Alternatively, if the test is iterating over a series of items, then the MRTS continues to administer the test until the test is administered a particular number of times or until the user provides a particular percentage (or number) of correct answers at a constant wait period. The goal of wait period is to trend toward some defined time depending on the goal. The goal of accuracy is to trend toward 100% (maximum) or the maximum capacity established in baseline testing.

In vanishing cues training, the MRTS provides the user with a prompt and target together. The user is asked to identify the target. When the user correctly identifies the target, one or more letters are removed. If the user then incorrectly identifies the target, one or more letters are added. This test continues until the user provides a correct answer given with no letters remaining (i.e., free recall), until the user provides a particular number of incorrect answers at the same level, or until the user provides a particular number of incorrect answers total. The goal of reaction time is to trend toward zero or immediate target identification (minimum) or the maximum capacity established in baseline testing. The goal of accuracy is to trend toward 100% (maximum) or the maximum capacity established in baseline testing. The goal of number of letters/cues needed is to trend toward zero cues needed (minimum) or the maximum capacity established in baseline testing.

In graduated cuing training, the MRTS provides the user with a prompt and asks the user for the target with no cue. If the user correctly identifies the target, the next prompt is provided. If the user incorrectly identifies the target, one or more letters are added. The test continues until the user correctly provides identification of the target or until all letters of the target have been revealed. The goal of reaction time is to trend toward zero or immediate target identification (minimum) or the maximum capacity established in baseline testing. The goal of accuracy is to trend toward 100% (maximum) or the maximum capacity established in baseline testing. The goal of number of letters/cues needed is to trend toward zero cues needed (minimum) or the maximum capacity established in baseline testing.

Scoring of cognitive testing/training methods can be performed in a variety of ways by the algorithm to determine a user's tested cognitive ability, which the algorithm ultimately compares to the user's baseline cognitive ability to personalize each test for each user. Free recall scoring can be performed by measuring the percent of targets correctly identified, reaction time, and total completion time. The algorithm tracks consistent successes, for example by item, subject, time of day, target, duration of exposure of each prompt, and duration of exposure of each target. The algorithm tracks consistent failures as well, for example by item, subject, time of day, target, duration of exposure of each prompt, and duration of exposure of each target. The algorithm also measures change in percent correct from a previous test, change in reaction time from a previous test, and change in total time from a previous test. Spaced retrieval scoring can be performed by measuring length of wait period before failure (i.e., incorrect identification of target), length of wait period required for success after experiencing failure, pattern of results after first failure, reaction time as a function of wait period, and change in results from a previous test. Vanishing cues scoring can be performed by measuring the number of cues that are removed before error, change in reaction time for an answer as a function of the number of cues provided, number of cues required for success after experiencing failure, and change in results from a previous test. Graduated cuing scoring can be performed by measuring the number of cues required for success after experiencing failure, change in reaction time for an answer as a function of the number of cues provided, and change in results from a previous test. The algorithm uses some or all of the foregoing measurements to automatically create the user's tested cognitive ability. The algorithm may also modify the testing parameters of the training methods administered to the user to obtain a larger test sample and determine the user's tested cognitive ability even more accurately.

The MRTS can maintain or monitor baseline cognitive ability over time by administering baseline tests at regular intervals. This helps determine the user's capacity for gain as well. Using the user's tested cognitive ability and baseline cognitive ability, the algorithm validates that the user's tested cognitive ability meets the assumptions and expectations of the user's baseline cognitive ability. If the user's tested cognitive ability meets the assumptions and expectations of his/her baseline cognitive ability, the user automatically continues along the same or similar testing pattern, though certain parameters may change to maintain originality of testing for the user. The user may meet the expectations of his/her baseline cognitive ability as determined by the algorithm, for example the user's tested cognitive ability approaching a certain level or goal.

If the user's tested cognitive ability does not meet (i.e., fails to meet or exceeds) the assumptions and expectations of his/her baseline cognitive ability, another baseline test is automatically scheduled to be administered to the user to more accurately reflect the assumptions and expectations of the user's baseline cognitive ability. Moreover, the user's personal goal is updated accordingly, which, in turn with the baseline cognitive ability, more accurately generates the cognitive testing/training methods administered to the user.

Additionally, during training, if a user is consistently identifying the targets of items correctly, then the items and testing automatically become harder, and, if necessary, the user's personal goal is updated. On the other hand, if the user is consistently identifying the targets of items incorrectly, then the items and testing automatically become easier, and, if necessary, the user's personal goal is updated. This is similar to computerized adaptive testing, disclosed by U.S. Pat. No. 5,657,256, which is hereby incorporated by reference.

Figure 7:
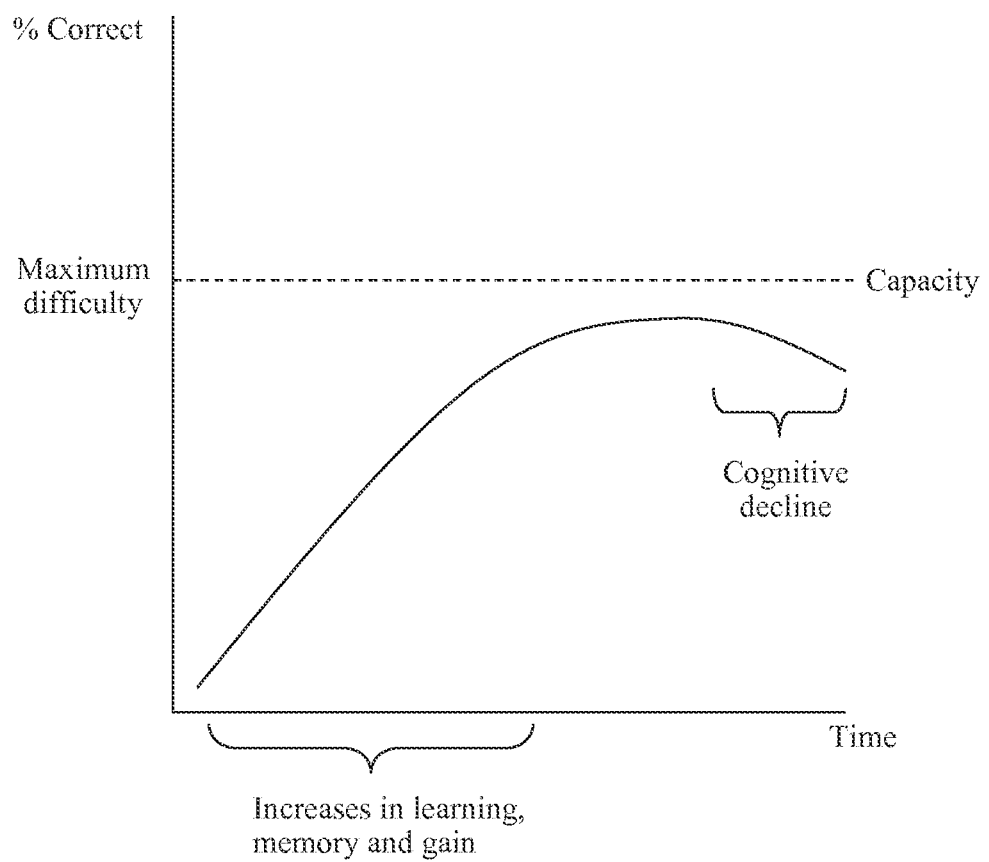
FIG. 7 depicts a graph illustrating total capacity of a user as a function of the user's correct answers over time.

As discussed, a user's personal goal can be maintained or updated based on the user's performance in cognitive testing. Typically, as depicted in FIG. 7, the user's goal can be increased (e.g., made more difficult) due to learning, can be decreased (e.g., made easier) due to cognitive decline, or remain fixed (e.g., made neither more difficult nor easier) while the user's performance and capacities (e.g., learning, memory, gain, reaction time) are updated through further baseline testing. A decline in testing (i.e., percent correct, reaction time, etc.) is an indicator of cognitive decline in the user. The algorithm can measure this decline and prompt changes in care, medication, doctor visits, etc. Thus, the algorithm can also automatically correct and personalize the user's cognitive testing accordingly based in the aforementioned factors.

Implementation of MRTS

Figure 5A:
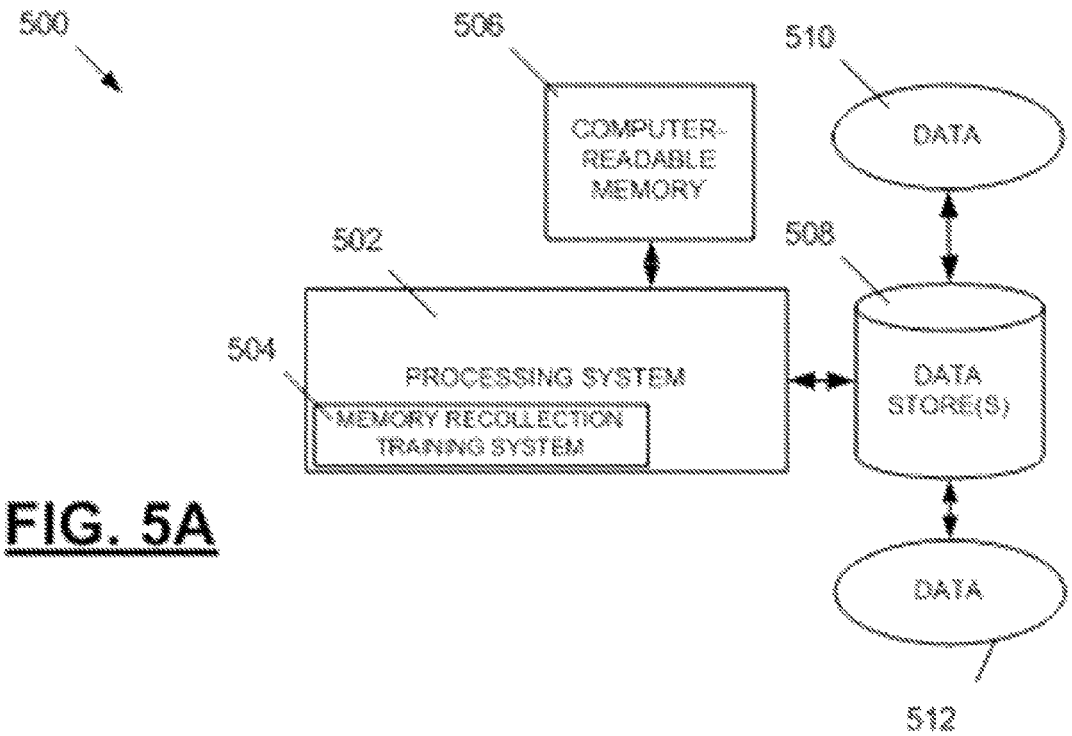
FIG. 5A depicts an example system for use in implementing a memory recollection training system.
Figure 5B:
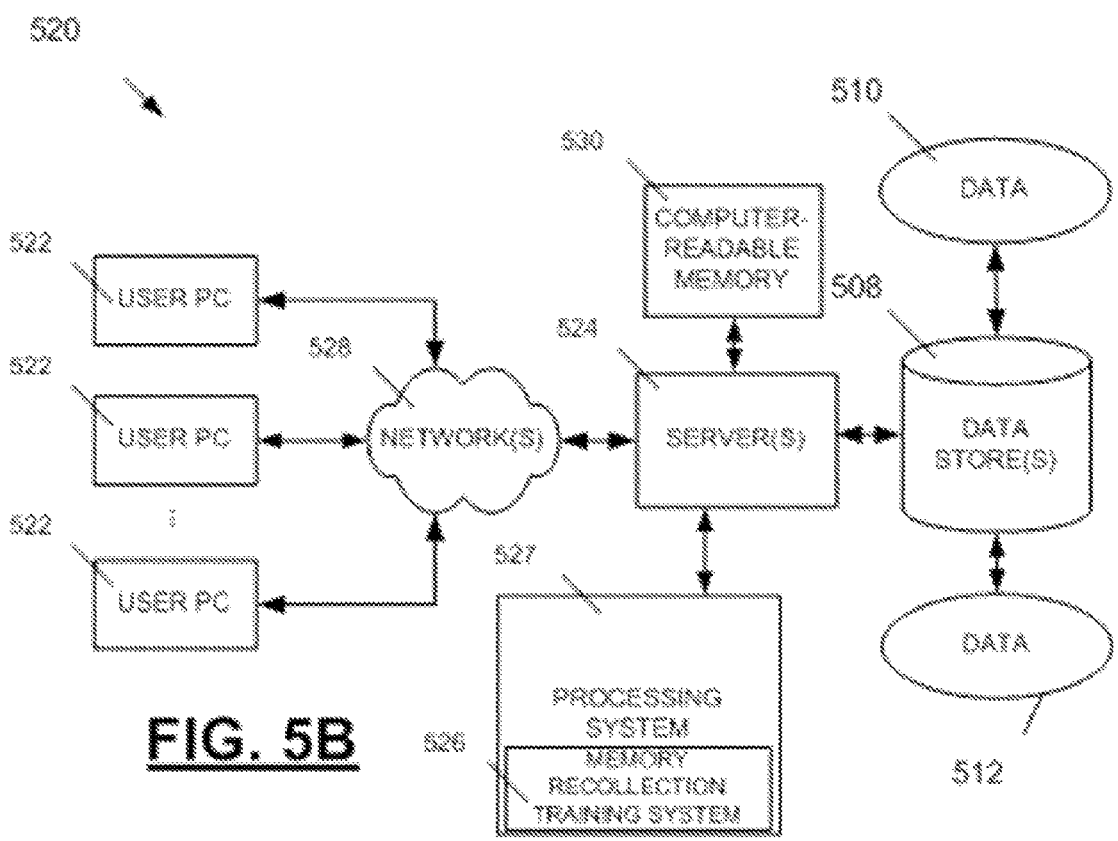
FIG. 5B depicts an example system for use in implementing a memory recollection training system.
Figure 5C:
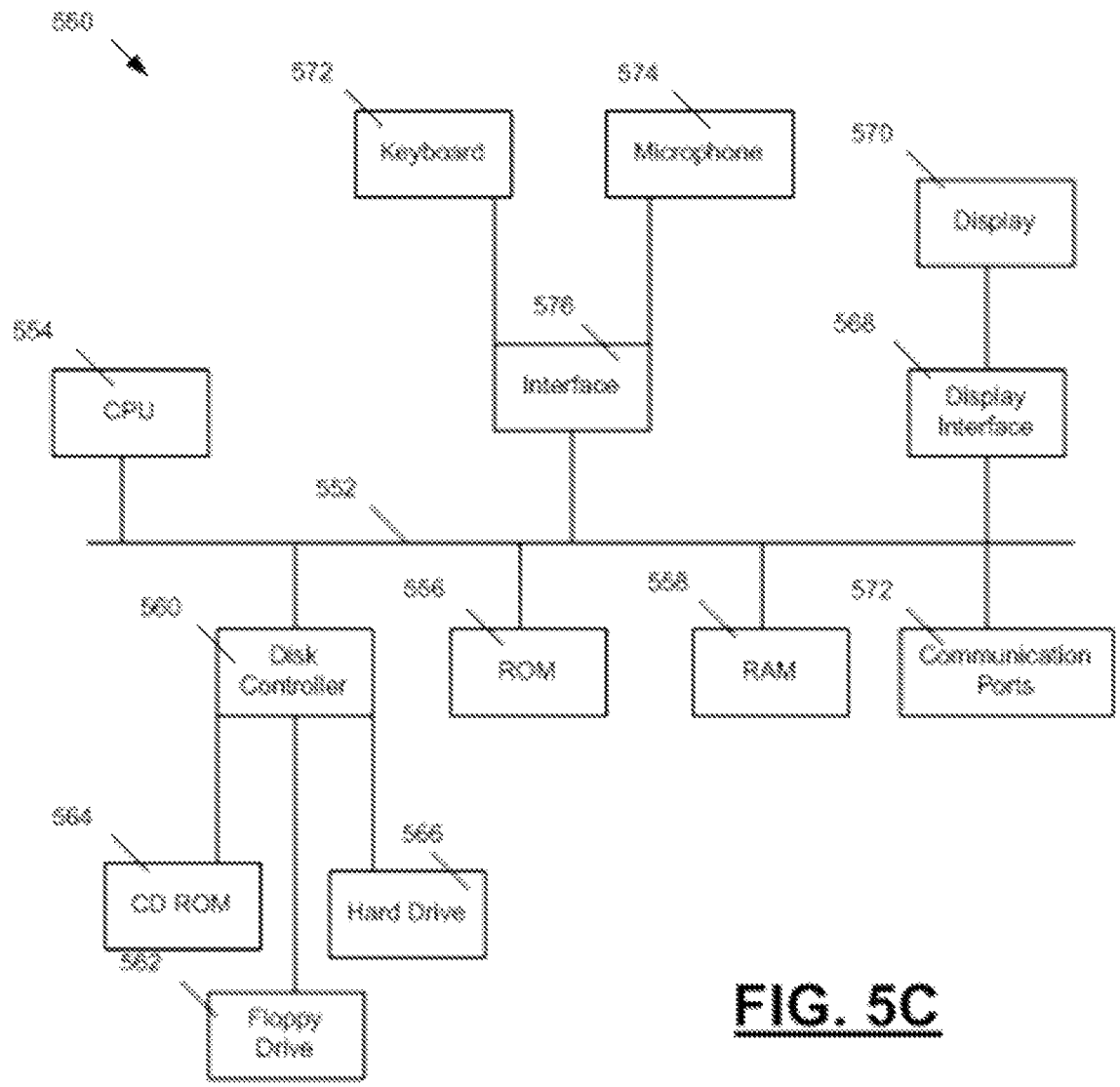
FIG. 5C depicts an example system for use in implementing a memory recollection training system.

FIGS. 5A, 5B and 5C depict example systems for use in implementing a memory recollection training system. For example, FIG. 5A depicts an exemplary system 500 that includes a standalone computer architecture where a processing system 502 (e.g., one or more computer processors) includes a memory recollection training system 504 being executed on it. The processing system 502 has access to a computer-readable memory 506 in addition to one or more data stores 508. The one or more data stores 508 may include a variety of data 510, 512.

FIG. 5B depicts a system 520 that includes a client server architecture. One or more user PCs 522 accesses one or more servers 524 running a memory recollection training system 526 on a processing system 527 via one or more networks 528. Alternatively, the one or more user PCs 522 can be any end-user device, such as a tablet, smart phone, or other electronic device. The one or more servers 524 may access a computer readable memory 530 as well as one or more data stores 532. The one or more data stores 532 a variety of data 534, 536.

FIG. 5C shows a block diagram of exemplary hardware for a standalone computer architecture 550, such as the architecture depicted in FIG. 5A that may be used to contain and/or implement the program instructions of system embodiments of the present invention. A bus 552 may serve as the information highway interconnecting the other illustrated components of the hardware. A processing system 554 labeled CPU (central processing unit) (e.g., one or more computer processors), may perform calculations and logic operations required to execute a program. A processor-readable storage medium, such as read only memory (ROM) 556 and random access memory (RAM) 558, may be in communication with the processing system 554 and may contain one or more programming instructions implementing a memory recollection training system. Optionally, program instructions may be stored on a computer readable storage medium such as a magnetic disk, optical disk, recordable memory device, flash memory, or other physical storage medium. Computer instructions may also be communicated via a communications signal, or a modulated carrier wave.

A disk controller 560 interfaces one or more optional disk drives to the system bus 552. These disk drives may be external or internal floppy disk drives such as 562, external or internal CD-ROM, CD-R, CD-RW or DVD drives such as 564, or external or internal hard drives 566. As indicated previously, these various disk drives and disk controllers are optional devices.

Each of the element managers, real-time data buffer, conveyors, file input processor, database index shared access memory loader, reference data buffer and data managers may include a software application stored in one or more of the disk drives connected to the disk controller 560, the ROM 556 and/or the RAM 558. Preferably, the processor 554 may access each component as required.

A display interface 568 may permit information from the bus 556 to be displayed on a display 570 in audio, graphic, or alphanumeric format. Communication with external devices may optionally occur using various communication ports 572.

In addition to the standard computer-type components, the hardware may also include data input devices, such as a keyboard 572, or other input device 574, such as a microphone, remote control, pointer, mouse, webcam and/or joystick.

As additional examples, for example, the systems and methods may include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, FLASH memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

Definition of Claim Terms

The term "access" is used herein to refer to the ability for an individual to retrieve specific information, wherein the user can retrieve the information if the user is determined to have sufficient cognitive ability (manually preset by authorized parties or automatically set by test algorithm). If the individual does not have this sufficient cognitive ability, the individual may be limited in retrieving or "accessing" the specific information. The specific information may include, for example, a phone number for a contact, email address for a contact, or photographs of a contact.

The term "allowable message parameters" is used herein to refer to conditions or characteristics required for a particular type of communication to be transmitted to a recipient. For example, a communicated transmitted to a recipient through TWITTER requires 140 characters or less.

The term "alternate method of communication" is used herein to refer to a medium of electronic communication that is used when a user does not meet the allowable message parameters of a primary method of communication. For example, if a primary method of communication is TWITTER and a message is over 140 characters in length, the message may be transmitted via FACEBOOK, email or other medium.

The term "baseline cognitive ability" is used herein to refer to the mental (i.e., logic, memory, etc.) capabilities of a user upon being administered one or more preliminary tests that provide the user with a prompt and ask the user for a target. Baseline cognitive ability is determined by the test algorithm and is based on the user's capacities for learning, memory, gain and reaction time.

The term "baseline test" is used herein to refer to a test administered to a user to determine the user's baseline cognitive ability. It can be any type of cognitive or memory test and any combination thereof, including, for example, a free recall test and/or graduated cuing test. Results and data (e.g., percent correct, reaction time, etc.) are gathered from the baseline test by the test algorithm to automatically determine the user's baseline cognitive ability and subsequent cognitive tests.

The term "baseline threshold" is used herein to refer to standards preset by authorized parties (i.e., manual) or set by the test algorithm (i.e., automated) for the baseline tests. A user's responses in the baseline tests are compared to the "baseline thresholds" to determine whether a user passes or fails the baseline tests. Passing the baseline tests (i.e., exceeding the baseline thresholds) indicates higher cognitive ability, and failing the baseline tests (i.e., failing to meet the baseline thresholds) indicates lower cognitive ability.

The term "capacity for learning" is used herein to refer to the ability for a user to freely recall targets within one testing session (i.e., over a shorter term period). For example, learning can be indicated by retention intervals from a couple seconds up to twenty minutes or longer, depending on the user's goal.

The term "capacity for memory" is used herein to refer to the ability for a user to freely recall targets between testing sessions (i.e., over a longer term period). For example, memory can be indicated by any retention levels beyond one training session, such as an hour, a day, a week, a month or longer, depending on the user's goal.

The term "capacity for gain" is used herein to refer to the user's speed of learning (within tests) and memory (between tests) over time. Typically, a user's "capacity for gain" is higher initially since the user is able to learn a lot. The capacity for gain may gradually decline as the user approaches his/her maximum potential.

The term "capacity for reaction time" is used herein to refer to the time needed for a user to identify, correctly or incorrectly, a target upon being provided a prompt and/or hint/cue.

The term "computer-implemented method" is used herein to refer to a procedure or series of instructions for software carried out on a personal computer, tablet, smart phone or other electronic device. The method may be performed via an algorithm that automatically determines the progress and cognitive capabilities of a user, and adjusts the testing accordingly.

As used herein, the term "cognitive test" and "memory training exercise" are used herein to refer to any training method administered to a user and personalized based on the user's baseline cognitive ability, personal goal and real-time performance within training Examples of training methods include, but are not limited to, free recall, graduated cuing, vanishing cues and spaced retrieval. However, each cognitive test has parameters that are modified and personalized to each user, and thus, each cognitive test is created via a unique combination of memory test techniques and performance parameters.

The term "computer-readable data store" is used herein to refer to an integrated data or information repository. An example includes various types of databases. This data repository can be read by a computer or other electronic device, and access (i.e., the ability for a user to transmit instructions to a computer to read the data or information therein) is limited based on certain standards. For example, access may be limited by the cognitive abilities of a user.

The term "conform" is used herein to refer to being in accordance with a set of specifications or guidelines. For example, if a message must "conform" with a set of parameters contained within a particular medium of communication, the message must contain parameters that are in accordance or align with the set of parameters contained within the particular medium of communication.

The term "connection" is used herein to refer to a communications link between two individuals or contacts. The "connection" can be personal, professional, or non-personal. Examples of connections include, but are not limited to, family members, friends, caregivers, colleagues, resident and carrier (i.e., mail, packages, etc.), and other individuals who have any occasion to interact with each other.

The term "contacts" is used herein to refer to individuals in a user's social network or individuals that the user may have any occasion to communicate with or receive communications from, either digitally or in person.

The term "cue" is used herein to refer to an intermediary stage between a prompt and a target for aiding a user in the proper identification of the target. Typically, a "cue" is a piece of information about the target. Examples of cues include, but are not limited to, letters, noises, video, or other sensory hints that helps the user correctly identify the target when given the prompt. The ultimate goal is to provide the user with zero cues, so the user can freely recall a target when given a prompt.

The term "data" is used herein to refer to information about individuals in a user's social network. This information includes, but is not limited to, an individual's name, photo, address, contact information, interests and disinterests, relationship to the user, or other relevant information about which the user should be or wishes to be knowledgeable.

The term "define" is used herein to refer to reinforcing, expressing, enhancing, describing, or displaying one or more pieces of information. For example, a contact can be defined in a user's address book or directory by a name, photo, or fact. What the contact is ultimately defined by can be preset by authorized parties or can be automatically determined based on the cognitive abilities of the user (e.g., what, if any, name, photo or fact is most recognizable to the user).

The term "difficulty" is used herein to refer to the relative level of ease or hardship of a cognitive test. Based on a user's responses when given prompts, a test algorithm can detect accuracy and reaction time in order to increase or decrease difficulty accordingly. For example, if a user provides consistently accurate answers, the test algorithm may increase "difficulty" of a spaced retrieval test by increasing the amount of time that the target is not shown to the user.

The term "digitized media prompt" is used herein to refer to a digital stimulus that is given to the end-user and is intended to trigger the end-user's identification of a target associated with the stimulus. It can be any audio or visual stimulus typically associated with an individual in the end-user's social network.

The term "diverge" is used herein to refer to not being in accordance with a set of specifications or guidelines. For example, if a message "diverges" from a set of parameters contained within a particular medium of communication, the message contains parameters that are not in accordance or do not align with the set of parameters contained within the particular medium of communication.

The term "expectations" is used herein to refer to results that a user is anticipated to provide and a cognitive ability that the user is anticipated to have upon undergoing one or more cognitive tests. For example, the user's baseline cognitive ability provides "expectations" of how the user will perform in cognitive tests. If expectations are not met, the user may undergo baseline tests again to re-assess expectations.

The term "fails to meet" is used herein to refer to a particular value being below or above a standard or set of expectations. For example, if a user's tested cognitive ability "fails to meet" the expectations set by the user's baseline cognitive ability, then the user's tested cognitive ability could exceed or fall below the expectations.

The term "free recall test" is used herein to refer to a training method wherein a test taker is shown a prompt and is asked to identify the target. In a pure free recall test, no cues are given. However, it is contemplated that the free recall test can be combined with other training methods, such as a graduated cuing test, to achieve particular goals of the test taker. A test algorithm can determine the item tested according to the cognitive ability of the user and according to the real-time answers provided by the user.

The term "goal" is used herein to refer to a result that a user is attempting to achieve by engaging the current invention. Goals are personal to each user since each user has a different cognitive ability and wishes to remember different items. For example, one user may wish to instantly remember the identity of his neighbor, while another user may wish to remember, for a 24-hour period, where she should put her keys, so that they are consistently in the same place.

The term "graduated cuing test" is used herein to refer to a training method wherein a test taker is shown a prompt and a target. Thereafter, the target disappears as the test taker is asked to identify the target. If the test taker incorrectly identifies the target or needs a hint/cue, one or more letters or other cues of the target are displayed to the test taker. This continues until the test taker correctly identifies the target. A test algorithm can determine the item tested and how many letters or cues are added according to the cognitive ability of the user and according to the real-time answers provided by the user.

The term "high cognitive ability" is used herein to refer to mental (i.e., logic) capabilities of a user as being elevated relative to the user's previous mental capabilities, relative to other users, or relative to a particular preset standard.

The term "individual" is used herein to refer to any end-user, operator or facilitator of the current invention. Examples include residents at assisted living facilities, sufferers of dementia, persons with suboptimal cognitive acuity, persons wishing to enhance or maintain cognitive ability, or persons in an end-user's social network, authorized parties or other individuals finding the current invention useful to achieve personal goals or objectives.

The term "memory recollection training" is used herein to refer to the assessing a user's maximum cognitive ability and exercising the user to achieve that maximum cognitive ability using a personalized, goal-oriented approach. This type of training can be conducted once or multiple times as a test algorithm adjusts the testing, personal goals and maximum cognitive ability of the user based on the progress of the user.

graduated cuing

The term "message" is used herein to refer to any type of electronic communication, for example including, but not limited to, social information message, email, voice message, text message, video, or other electronic medium.

The term "modify" is used herein to refer to the test algorithm's automatic altering of any aspect of a user's training For example, the user's personal goal and parameters of a baseline/cognitive test can be modified by the test algorithm based on the user's performance through the cognitive tests.

The term "parameters" is used herein to refer to a variable that is kept constant throughout a particular test or stage of the particular test thereof. Parameters depend on the type of test being administered but may include, though not limited to, time allowed to identify a target, number and type of cues provided, number and type of items tested, or other variable that affects a user's test-taking experience. It is assumed that administering a test with a set of parameters, followed by administering a test with a varied set of parameters, provides a more accurate assessment of a user's cognitive ability.

The term "performance" is used herein to refer to a user's ongoing execution of a training test administered to the user. A "performance" generally tends toward being considered unsuccessful if a user incorrectly identifies targets, while the "performance" generally tends toward being successful if the user correctly identifies targets. A test algorithm can adjust current testing, baseline cognitive abilities and personal goals of the user in real-time based on the "performance" of the user in identifying targets.

The term "periodically" is used herein to refer to the administration of training methods or baseline tests in repeated cycles, regular intervals or random intervals but still repeatedly. Administering tests "periodically" to a user allows measurement of the user's ability to learn or gain cognitive ability. Additionally, it allows a test algorithm to adjust testing, baseline cognitive abilities and personal goals according to the tested cognitive ability of the user, which is measured by administration of tests to the user.

The term "preferred method of communication" is used herein to refer to a primary medium of electronic communication preselected by an authorized party. Thus, when a user composes a message and transmits the message to the authorized party, the message is sent in the "preferred method of communication." The message must meet the allowable message parameters of the preferred method of communication. Otherwise, the message is sent via an alternate method of communication.

The term "prompt" is used herein to refer to the stimulus that is given to the user. Examples of prompts include, but are not limited to, a photograph of an individual, a video of an individual, the sound of an individual's voice, an illustration of an old memory, or other stimulus that the user can be used to signify a target. The goal of training is to reinforce the association between two or more stimuli, at least one prompt and at least one target.

The term "recall" is used herein to refer to the ability to retrieve a target and identify that target.

The term "re-establish" is used herein to refer to form, found, institute or confirm a preexisting connection between two individuals. For example, if an end-user has suboptimal cognitive acuity, a preexisting connection between the end-user and an individual in the end-user's social network may be lost. A goal of certain embodiments of the current invention is to re-form or re-confirm this connection to enhance communications between the end-user and the individual.

The term "response" is used herein to refer to a user's identification of targets, whether correct or incorrect, or non-identification of any targets, essentially any answer given by the user to a prompt.

The term "social network" is used herein to refer to a group of individuals with which a user communicates, individuals who the user wishes to identify, individuals who communicate with the user, and/or individuals who are associated with the user. A user's social network includes, but is not limited to, the user himself/herself, friends, family, educators, staff members implementing MRTS, assisted living facility staff, other residents in an assisted living facility and/or other authorized parties. A user's social network may have access to the user's directory, exercise portal, MRTS, etc.

The term "social information" is used herein to refer to a social structure made up of and interconnecting a plurality of individuals or organizations where the social structure is an interface for the transmission or exchange of data. Examples of "social information" structures include, but are not limited to, FACEBOOK, TWITTER, SKYPE, FLICKR, YOUTUBE, GOOGLE+, LINKEDIN, MEETUP, and FOURSQUARE.

The term "spaced retrieval test" is used herein to refer to a training method wherein a test taker is shown a prompt and a target. Thereafter, the target, and optionally the prompt, disappears as the test taker is asked to identify the target after a period of time. If the user correctly identifies the target, the test may move onto the next item. If the user incorrectly identifies the target, the test may move onto the next item or begin providing cues according to other training methods. As a user successfully identifies targets, the period of time may increase until the user is able to freely recall the target.

The term "suboptimal cognitive acuity" is used herein to refer to any mental (i.e., logic) ability that is lower than a user's maximum ability. Administering baseline and cognitive tests enables a user's cognitive acuity to be assessed and trained to reach maximum ability or maintain cognitive ability.

The term "target" is used herein to refer to the stimulus that is the object of identification for a user. Examples of targets include, but are not limited to, names of individuals in the user's social network, timing for meals, memories of facts, placement of objects, or other stimulus that the user can be trained to remember when given a prompt. The goal of training is to reinforce the association between two or more stimuli, at least one prompt and at least one target.

The term "tested cognitive ability" is used herein to refer to the mental (i.e., logic) acuity of a user upon being administered one or more cognitive tests. As the user progresses through training, the user's "tested cognitive ability" should approach the user's maximum capabilities, at which point the user may undergo baseline tests and cognitive tests to determine an updated tested cognitive ability, which is designed to meet expectations set forth by the user's baseline cognitive ability.

The term "total capacity" is used herein to refer to a combination of a user's capacities for memory, learning, gain and/or reaction time. A user's "total capacity" is used by the test algorithm to determine the user's baseline cognitive ability.

The term "vanishing cues test" is used herein to refer to a training method wherein a test taker is shown a prompt and a target. Thereafter, one or more letters or other cues of the target disappear as the test taker is asked to identify the target. If the test taker correctly identifies the target, more letters or cues disappear until the test taker correctly identifies the target with no letters of the target displayed. If the test taker incorrectly identifies the target, letters or cues can be added/displayed accordingly. A test algorithm can determine the item tested and how many or what percentage of letters or cues disappear and are added according to the cognitive ability of the user and according to the real-time answers provided by the user.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A computer-implemented software application, the software accessible from a non-transitory media and providing instructions for a computer processor to generate personalized memory recollection training indicia on a computer display for a first individual with suboptimal cognitive acuity, the instructions comprising:
   accessing a digitized media prompt associated with a second individual, said prompt selected from the group consisting of video, image, and audio files, wherein said prompt facilitates re-establishing a connection between said first individual and said second individual;
   receiving a cognitive objective;
   administering one or more baseline tests to said first individual for assessing a total capacity of said first individual, said one or more baseline tests including said digitized media prompt and a plurality of testable criteria;
   receiving responses to said one or more baseline tests from said first individual;
   determining a capacity for learning of said first individual and a capacity for memory of said first individual, said capacity for learning and said capacity for memory based on said responses to said one or more baseline tests received from said first individual;
   determining a cognitive baseline of said first individual based on said capacity for learning and said capacity tier memory, said cognitive baseline communicating expectations of a cognitive ability of said first individual;
   automatically generating a cognitive test based on said cognitive objective; and said cognitive baseline;
   administering said cognitive test to said first individual for training said first individual to said total capacity of said first individual;
   receiving responses to said cognitive test from said first individual;
   determining a tested cognitive ability of said first individual based on said responses to said cognitive test received from said first individual;
   equating said tested cognitive ability to said cognitive baseline;
   automatically re-administering said one or more baseline tests as a result of said tested cognitive ability failing to meet said expectations of said cognitive baseline upon being administered one or more of said cognitive test, followed by automatically re-generating said cognitive test based on said cognitive objective and a cognitive baseline determined from said re-administered one or more baseline tests.

2. A computer-implemented software application as in claim 1, further comprising instructions for:
   modifying said cognitive objective personal to said first individual as a result of said tested cognitive ability failing to meet said expectations of said cognitive baseline, followed by automatically re-generating said cognitive test based on said modified cognitive objective and said cognitive baseline.

3. A computer-implemented software application as in claim 1, further comprising instructions for:
   modifying testing parameters of said cognitive test; and
   administering said cognitive test to said first individual prior to determining said tested cognitive ability, whereby a more accurate tested cognitive ability may be determined.

4. A computer-implemented software application as in claim 1, further comprising instructions for:

determining a capacity for gain of said first individual, said capacity for gain based on said responses to said one or more baseline tests received from said first individual when said one or more baseline tests includes more than one baseline tests;

wherein said cognitive baseline is further based on said capacity for gain.

5. A computer-implemented software application as in claim 1, further comprising instructions for:

determining a capacity for reaction time of said first individual, said capacity for reaction time based on said responses to said one or more baseline tests received from said first individual;

wherein said cognitive baseline is further based on said capacity for reaction time.

6. A computer-implemented software application as in claim 1, further comprising:

said one or more baseline tests being one baseline test having a first series and a second series;

administering said first series of said baseline test to said first individual;

said first series including at least one training method from the group consisting of free recall, graduated cuing, vanishing cuing, and spaced retrieval;

administering said second series of said baseline test to said subject;

said second series being substantially similar to said first series;

determining said capacity for learning of said first individual based on differences in performance by said first individual between said first series and said second series.

7. A computer-implemented software application as in claim 1, further comprising instructions for:

administering said one or more baseline tests periodically, whereby said cognitive baseline of said first individual can be updated.

8. A computer-implemented software application as in claim 1, further comprising instructions for:

modifying testing parameters of said cognitive test to a higher difficulty as a result of said first individual consistently identifying targets within said cognitive test correctly; and modifying testing parameters of said cognitive test to a lower difficulty as a result of said first individual consistently identifying targets within said cognitive test incorrectly;

modifying said cognitive objective as a result of said first individual's correct or incorrect identifications of said targets.

9. A computer-implemented software application as in claim 1, further comprising:

said tested cognitive ability being a first tested cognitive ability;

determining a second tested cognitive ability of said first individual based on responses to a subsequent cognitive test received from said first individual said second tested cognitive ability indicating a cognitive decline in said first individual when said second tested cognitive ability has a lower value than said first tested cognitive ability.

10. A computer-implemented method of providing personalized memory recollection training to a first individual having suboptimal cognitive acuity, said method comprising the steps of:

receiving and storing data associated with each of a plurality of members of a social network of said first individual;

providing a first baseline memory test to said first individual;

comparing results of said first baseline memory test as provided by said first individual to a set of baseline thresholds;

determining whether said first individual passes or fails said first baseline memory test, said determination based on said comparison between said results of said first baseline memory test and said set of baseline thresholds, wherein said first individual passes said first baseline memory test when said results of said first baseline memory test exceed said set of baseline thresholds and said first individual fails said first baseline memory test when said set of baseline thresholds exceeds said results of said first baseline memory test, said first individual determined to have high cognitive ability when said first individual passes said first baseline memory test;

automatically providing a second baseline memory test to said first individual as a result of said first individual failing said first baseline memory test;

comparing results of said second baseline memory test as provided by said first individual to said set of baseline thresholds;

determining whether said first individual passes or fails said second baseline memory test, said determination based on said comparison between said results of said second baseline memory test and said set of baseline thresholds, wherein said first individual passes said second baseline memory test when said results of said second baseline memory test exceed said set of baseline thresholds and said first individual fails said second baseline memory test when said set of baseline thresholds exceeds said results of said second baseline memory test;

wherein a cognitive baseline of said first individual is determined based on said results of said first baseline memory test and said second baseline memory test;

administering a memory training exercise to said first individual, wherein difficulty of said memory training exercise is based on said determined cognitive baseline of said first individual, wherein said memory training exercise utilizes said data of a member of said social network selected from said plurality of members of said social network to provide said memory recollection training to improve an ability of said first individual to recall said member of said social network of said first individual.

11. A computer-implemented method as in claim 10, further comprising the step of:

administering a second memory training exercise to said first individual, wherein parameters of said second memory training exercise are automatically established based on results retrieved from said administered memory training exercise, wherein said memory training exercise utilizes said data of a second member of said social network selected from said plurality of members of said social network to provide said memory recollection training to improve an ability of said first individual to recall said second member of said social network of said first individual.

12. A computer-implemented method as in claim 10, further comprising:

said data including a name and a photograph of said member of said social network.

13. A computer-implemented method as in claim 10, further comprising:
   said data stored in a computer-readable data store;
   access to said data by said first individual limited based on said determined cognitive baseline of said first individual.

14. A computer-implemented method as in claim 10, further comprising:
   said first baseline memory test being a free recall test.

15. A computer-implemented method as in claim 14, further comprising:
   said second baseline memory test selected from the group consisting of a graduated cuing test, a vanishing cues test, and a spaced retrieval test;
   said selection of said second baseline memory test based on said results of said first baseline memory test.

16. A computer-implemented method as in claim 10, further comprising:
   said determined cognitive baseline of said first individual adjusted based on performance in said memory training exercise.

17. A computer-implemented method as in claim 10, further comprising the step of:
   administering said memory training exercise periodically to said first individual.

\* \* \* \* \*

UNITED STATES PATENT AND TRADEMARK OFFICE
CERTIFICATE OF CORRECTION

PATENT NO. : 8,814,359 B1
APPLICATION NO. : 13/447877
DATED : August 26, 2014
INVENTOR(S) : Daniel V. Pompilio, III et al.

Page 1 of 1

It is certified that error appears in the above-identified patent and that said Letters Patent is hereby corrected as shown below:

In the Claims,

Column 24, Claim 1, Line 28 should read:

based on said capacity for learning and said capacity for

Signed and Sealed this
Eighteenth Day of November, 2014

Michelle K. Lee
*Deputy Director of the United States Patent and Trademark Office*